United States Patent
Zhu

(10) Patent No.: US 11,560,559 B2
(45) Date of Patent: Jan. 24, 2023

(54) INDUCING PRODUCTION OF FULL-LENGTH PROGRANULIN (GRN) FROM NUCLEOTIDES INCLUDING MUTATIONS CONTAINING A PREMATURE STOP CODON (PTC)

(71) Applicant: University of Kentucky Research Foundation, Lexington, KY (US)

(72) Inventor: Haining Zhu, Lexington, KY (US)

(73) Assignees: University of Kentucky Research Foundation, Lexington, KY (US); The United States as Represented by The Dept of Veteran Affairs (VA), Washington, DC (US)

( * ) Notice: Subject to any disclaimer, the term of this patent is extended or adjusted under 35 U.S.C. 154(b) by 331 days.

(21) Appl. No.: 16/717,972

(22) Filed: Dec. 17, 2019

(65) Prior Publication Data

US 2020/0199571 A1 Jun. 25, 2020

Related U.S. Application Data

(60) Provisional application No. 62/780,801, filed on Dec. 17, 2018.

(51) Int. Cl.
*C12N 15/10* (2006.01)
*A61K 31/7036* (2006.01)

(52) U.S. Cl.
CPC ........ *C12N 15/102* (2013.01); *A61K 31/7036* (2013.01)

(58) Field of Classification Search
CPC .......................... C12N 15/102; A61K 31/7036
USPC ....................................................... 435/70.3
See application file for complete search history.

(56) References Cited

U.S. PATENT DOCUMENTS

| 7,928,068 | B2 | 4/2011 | Chuanju et al. |
| 2010/0324127 | A1 | 12/2010 | Kay et al. |
| 2014/0356321 | A1 | 12/2014 | Tim et al. |
| 2018/0177812 | A1 | 6/2018 | Baasav et al. |
| 2018/0258123 | A1 | 9/2018 | Roberge et al. |

FOREIGN PATENT DOCUMENTS

WO WO 2008/019187 * 2/2008

OTHER PUBLICATIONS

Howard et al. Sequence Specificity of Aminoglycoside-Induced Stop Codon Readthrough: Potential Implications for Treatment of Duchenne Muscular Dystrophy. Ann Neurol 2000;48:164-169. (Year: 2000).*

Cruts, M., Gijselinck, I., van der Zee, J., Engelborghs, S., Wils, H., Pirici, D., Rademakers, R., Vandenberghe, R., Dermaut, B., Martin, J.J. et al. (2006) Null mutations in progranulin cause ubiquitin-positive frontotemporal dementia linked to chromosome 17q21. Nature, 442, 920-924.

Rohrer, J.D., Guerreiro, R., Vandrovcova, J., Uphill, J., Reiman, D., Beck, J., Isaacs, A.M., Authier, A., Ferrari, R., Fox, N.C. et al. (2009) The heritability and genetics of frontotemporal lobar degeneration. Neurology, 73, 1451-1456.

Van Langenhove, T., van der Zee, J. and Van Broeckhoven, C. (2012) The molecular basis of the frontotemporal lobar degeneration-amyotrophic lateral sclerosis spectrum. Annals of medicine, 44, 817-828.

Chitramuthu, B.P., Bennett, H.P.J. and Bateman, A. (2017) Progranulin: a new avenue towards the understanding and treatment of neurodegenerative disease. Brain, 140, 3081-3104.

Nguyen, A.D., Nguyen, T.A., Zhang, J., Devireddy, S., Zhou, P., Karydas, A.M., Xu, X., Miller, B.L., Rigo, F., Ferguson, S.M. et al. (2018) Murine knockin model for progranulin-deficient frontotemporal dementia with nonsense-mediated mRNA decay. Proc Natl Acad Sci U S A, 115, E2849-E2858.

Arrant, A.E., Onyilo, V.C., Unger, D.E. and Roberson, E.D. (2018) Progranulin Gene Therapy Improves Lysosomal Dysfunction and Microglial Pathology Associated with Frontotemporal Dementia and Neuronal Ceroid Lipofuscinosis. J Neurosci, 38, 2341-2358.

Howard, M., Frizzell, R.A. and Bedwell, D.M. (1996) Aminoglycoside antibiotics restore CFTR function by overcoming premature stop mutations. Nat Med, 2, 467-469.

Howard, M.T., Anderson, C.B., Fass, U., Khatri, S., Gesteland, R.F., Atkins, J.F. and Flanigan, K.M. (2004) Readthrough of dystrophin stop codon mutations induced by aminoglycosides. Ann Neurol, 55, 422-426.

Lai, C.H., Chun, H.H., Nahas, S.A., Mitui, M., Gamo, K.M., Du, L. and Galli, R.A. (2004) Correction of ATM gene function by aminoglycoside-induced read-through of premature termination codons. Proc Natl Acad Sci U S A, 101, 15676-15681.

Kuschal, C., DiGiovanna, J.J., Khan, S.G., Gatti, R.A. and Kraemer, K.H. (2013) Repair of UV photolesions in xeroderma pigmentosum group C cells induced by translational readthrough of premature termination codons. Proc Natl Acad Sci U S A, 110, 19483-19488.

Pitcher, M.R., Herrera, J.A., Buffington, S.A., Kochukov, M.Y., Merritt, J.K., Fisher, A.R., Schanen, N.C., Costa-Mattioli, M. and Neul, J.L. (2015) Rett syndrome like phenotypes in the R255X Mecp2 mutant mouse are rescued by MECP2 transgene. Hum Mol Genet, 24, 2662-2672.

Lincoln, V., Cogan, J., Hou, Y., Hirsch, M., Hao, M., Alexeev, V., De Luca, M., De Rosa, L., Bauer, J.W., Woodley, D.T. et al. (2018) Gentamicin induces LAMB3 nonsense mutation readthrough and restores functional laminin 332 in functional epidermolysis bullosa. Proc Natl Acad Sci USA, 115, E6536-e6545.

(Continued)

*Primary Examiner* — Yih-Horng Shiao
(74) *Attorney, Agent, or Firm* — Stites & Harbison PLLC; Mandy Wilson Decker

(57) ABSTRACT

Disclosed herein are methods for inducing production of full-length progranulin (GRN) from a nucleotide encoding a GRN with a premature stop codon (GRN-PTC), comprising exposing the GRN-PTC to an aminoglycoside. Methods for inducing production of full-length progranulin (GRN) from a nucleotide encoding a GRN with a premature stop codon (GRN-PTC), comprising administering gentamicin or G418 is also disclosed.

7 Claims, 8 Drawing Sheets

Specification includes a Sequence Listing.

(56) References Cited

OTHER PUBLICATIONS

Karijolich, J. and Yu, Y.T. (2014) Therapeutic suppression of premature termination codons: mechanisms and clinical considerations (review). Int J Mol Med, 34, 355-362.
Welch, E.M., Barton, E.R., Zhuo, J., Tomizawa, Y., Friesen, W.J., Trifillis, P., Paushkin, S., Patel, M., Trotta, C.R., Hwang, S. et al. (2007) PTC124 targets genetic disorders caused by nonsense mutations. Nature, 447, 87-91.
Namgoong, J.H. and Bertoni, C. (2016) Clinical potential of ataluren in the treatment of Duchenne muscular dystrophy. Degener Neurol Neuromuscul Dis, 6, 37-48.
Chen, et al, Progranulin associates with hexosaminidase A and ameliorates GM2 ganglioside accumulation and lysosomal storage in Tay-Sachs disease, Journal of Molecular Medicine, 2018. pp. 2-16.
Kleinberger, et al., Mechanisms of Granulin Deficiency: Lessons from Cellular and Animal Models, Mol Neurobiol (2013) 47:337-360.
Vossel, et al., New Approaches to the Treatment of Frontotemporal Lobar Degeneration, Curr Opin Neurol. Dec. 2008; 21(6): 708-716.

* cited by examiner

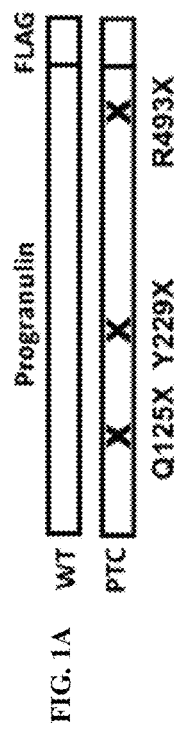
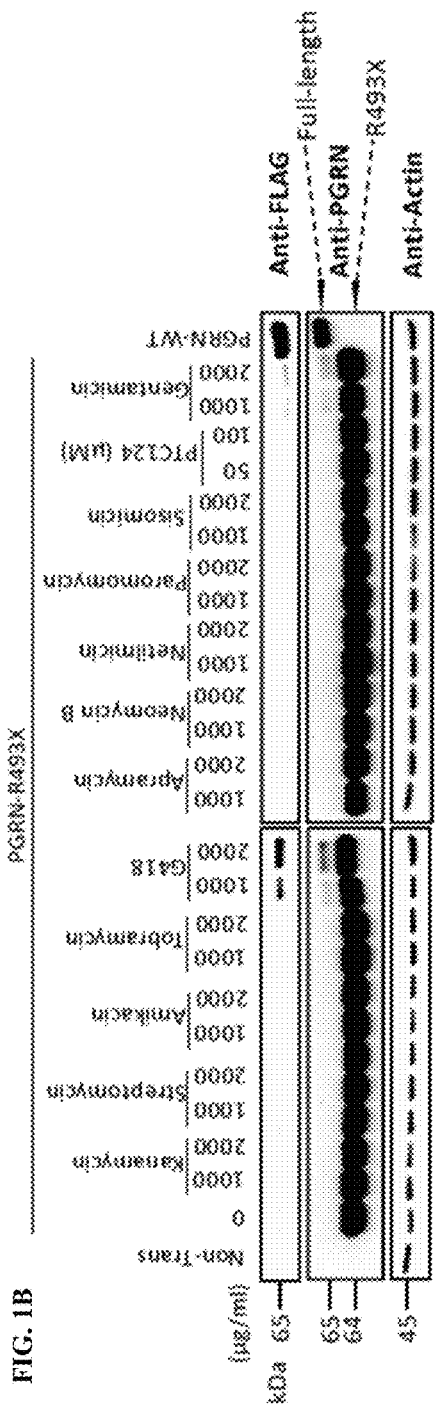
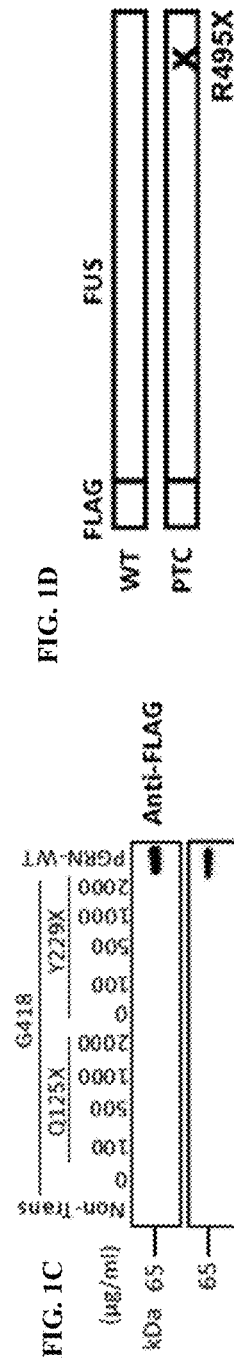
FIG. 1A
FIG. 1B
FIG. 1C
FIG. 1D

INDUCING PRODUCTION OF FULL-LENGTH PROGRANULIN (GRN) FROM NUCLEOTIDES INCLUDING MUTATIONS CONTAINING A PREMATURE STOP CODON (PTC)

RELATED APPLICATIONS

This application claims priority from U.S. Provisional Patent Application No. 62/780,801 filed on Dec. 17, 2018, the entire disclosure of which is incorporated herein by this reference.

GOVERNMENT INTEREST

This invention was made with government support under grant numbers R01 NS077284 and R01NS070899 awarded by the National Institutes of Health and grant number 101 BX002149 awarded by the Department of Veterans Affairs. The government has certain rights in the invention.

TECHNICAL FIELD

The presently-disclosed subject matter generally relates to progranulin-mediated familial frontotermporal dementia. In particular, certain embodiments of the presently-disclosed subject matter relate to inducing production of full-length progranulin (GRN) from nucleotides encoding GRN, which include mutations containing a premature stop codon.

BACKGROUND AND SUMMARY

The present invention tested several aminoglycosides in a cell culture system to determine whether read-through of nonsense mutations of GRN can be induced and to promote the production of full-length GRN protein. Two compounds rescued the expression of full-length GRN protein carrying the R493X PTC: gentamicin (an FDA-approved antibiotic) and a similar compound geneticin (or called G418). Data are presented below.

Frontotemporal dementia (FTD, also known as frontotemporal lobar dementia or FTLD) is a clinically and pathologically heterogeneous group of non-Alzheimer dementias characterized by progressive atrophy of the frontal and/or temporal lobes (1). FTD is characterized by gradual impairment of cognitive and language skills as well as personality and behavioral changes. It is the second most common dementia after Alzheimer's disease (2). FTD is highly heritable with approximately 35-50% familial cases (3, 4). Several genetic mutations have been identified that cause FTD or related disorders, including mutations in the C9ORF72 (5), Fused in Sarcoma (FUS) (6), microtubule-associated protein tau (MAP7) (3), and progranulin (GRN) genes (3, 5, 7). Pathogenic mutations in progranulin were detected in ~10% of FTD cases and ~22% in familial FTD cases (8). FTD is the most common form of dementia for people under age 60. Currently, there is no known treatment to prevent or stop FTD.

Human progranulin encodes a 593 amino acid protein involved in many biological processes including development (9), wound repair (10), and neuroinflammation (11-13). Progranulin is localized in endosomes, Golgi (14) and lysosome, and it likely participates in endocytosis, secretion and lysosomal functions (15, 16). However, the molecular function of progranulin under physiological and pathological conditions remain to be defined. Many FTD-causing mutations in progranulin are nonsense mutations with a premature termination codon (PTC) that result in a truncated protein. Consequently, haploinsufficiency of functional progranulin has been proposed as a major contributor to FTD. Knockout (17) and knock-in (18) animal models demonstrated that progranulin haploinsufficiency cause FTD pathology. Additionally, restoring progranulin levels improved preexisting FTD pathology in progranulin deficient mice (19). The homozygous knockout caused lysosomal dysfunction similar to those observed in the human lysosomal storage disease neuronal ceroid lipofuscinosis (NCL), which was also partially rescued by restoring progranulin levels (19). Together, these results support the notion that restoring progranulin expression can be an effective therapeutic approach.

Aminoglycosides are a class of gram-negative bacilli antibiotics that function by binding to bacterial ribosomes and interfering with protein translation (20). A lesser known function of aminoglycosides is to induce the eukaryotic protein translation machinery to read-through PTC mutations and yield a full-length protein. The aminoglycoside-induced read-through strategy has been utilized in multiple diseases caused by PTC mutation, including cystic fibrosis (21, 22), Duchenne muscular dystrophy (DMD) (23), ataxia-telangiectsia (24), Rett's syndrome (25, 26), and most recently junctional epidermolysis bullosa (27). Partial restoration of protein expression resulting from PTC read-through has been demonstrated in in vitro assays, cell culture systems, mouse models, and human patients (28, 29). Although aminoglycosides have some potential side effects, such as impairment of mitochondrial translation in eukaryotic cells, their ability of inducing PTC read-through has raised the possibility of treating human diseases caused by PTCs. Moreover, the new read-through compound PTC124 (or ataluren) displayed beneficial effects in clinical trials (30) and was clinically approved to treat DMD in Europe in 2014.

Eleven aminoglycosides were screened and PTC124 in a cell culture system to determine whether any compound can induce read-through of progranulin PTC mutations in FTD or a FUS PTC mutation in the related neurodegenerative disease amyotrophic lateral sclerosis (ALS). The aminoglycosides gentamicin and G418 (also known as geneticin) specifically rescued expression of the R493X mutation of progranulin but not other progranulin or FUS PTC mutations. G418 rescued R493X expression to nearly 50% of wild-type (WT) progranulin while gentamicin rescued less than 10%. The read-through effect was dose and time-dependent. Strikingly, the read-through protein displayed similar subcellular localization patterns as WT progranulin. These results provide a proof-of-principal that aminoglycosides, or other compounds promoting progranulin PTC read-through, could be an exciting therapeutic avenue for familial FTD caused by progranulin nonsense mutations.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Although any methods, devices, and materials similar or equivalent to those described herein can be used in the practice or testing of the presently-disclosed subject matter, representative methods, devices, and materials are described herein.

The presently-disclosed subject matter is further illustrated by the following specific but non-limiting examples. The following examples may include compilations of data that are representative of data gathered at various times during the course of development and experimentation related to the present invention.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

FIG. 1A shows G418 and gentamicin induced readthrough of progranulin PTC mutation R493X. Schematic diagram of WT progranulin and PTC mutations examined in this study. Each construct has a C-terminal FLAG tag.

FIG. 1B shows G418 and gentamicin induced readthrough of progranulin PTC mutation R493X. Examination of potential readthrough effect of 11 aminoglycosides and PTC124 on R493X proganulin. N2A cells were transfected with WT or R493X proganulin, allowed to recover, and treated with two different concentrations of each compound for 24 hours. Cell lysates were generated, separated by SDS-PAGE, and analyzed by Western analysis using anti-FLAG (top), anti-progranulin (middle), and anti-actin (lower) antibodies. Among 12 compounds tested, only G418 and gentamicin induced FLAG bands, demonstrating positive readthrough effect. WT progranulin was included as a positive control. No transfection or no compound treatment were included as negative controls. For the anti-progranulin blot, the lower band is the R493X truncated protein and the higher band is full-length progranulin.

FIG. 1C shows G418 and gentamicin induced readthrough of progranulin PTC mutation R493X. G418 had no readthrough effect on two other FTD mutations Q125X and Y229X. No full-length readthrough protein was observed in the FLAG blot. In the anti-progranulin blot, the higher band is WT progranulin and the lower band is the Q229Y truncated protein. The Q125X truncated protein was visible with longer exposure.

FIG. 1D shows G418 and gentamicin induced readthrough of progranulin PTC mutation R493X. Examination of G418 on the R495X mutation of FUS responsible for familial ALS. WT or R495X FUS was tagged with FLAG at the N-terminus. N2A cells were transfected with WT or R495X FUS, allowed to recover, and treated with three concentrations of G418 for 24 hours. Cells were harvested and cell lysates were subjected to SDS-PAGE and Western analysis using anti-FLAG (top) and anti-actin (lower) antibodies. The slightly higher band is WT FUS and the lower band is R495X truncated FUS. G418 did not induce readthrough of R495X FUS.

Figure 2A:
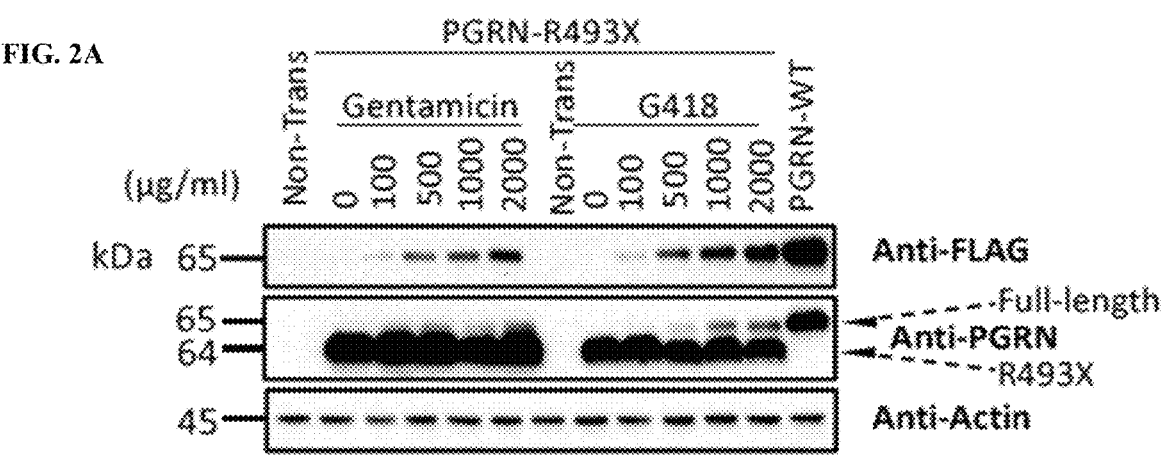
FIG. 2A. shows G418 and gentamicin induced dose-dependent R493X progranulin readthrough. Gentamicin and G418 induced readthrough of progranulin R493X in a dose-dependent manner. N2A cells were transfected with WT or R493X proganulin, allowed to recover, and treated with increasing concentrations of G418 or gentamicin for 24 hours. Cell lysates were generated, separated by SDS-PAGE, and analyzed by Western analysis using anti-FLAG (top), anti-progranulin (middle), and anti-actin (lower) antibodies. For the anti-progranulin blot, the lower band is the R493X truncated protein and the higher band is full-length progranulin.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DESCRIPTION OF EXEMPLARY EMBODIMENTS

Definitions

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9):1726-1732).

Although any methods, devices, and materials similar or equivalent to those described herein can be used in the practice or testing of the presently-disclosed subject matter, representative methods, devices, and materials are described herein.

Following long-standing patent law convention, the terms "a", "an", and "the" refer to "one or more" when used in this application, including the claims. Thus, for example, reference to "a device" includes a plurality of such devices, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±10%, in some embodiments ±5%, in some embodiments ±1%, in some embodiments ±0.5%, in some embodiments ±0.1%, and in some embodiments ±0.01% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the term "subject" refers to a target in need of a diagnosis. The subject of the herein disclosed methods can be a mammal. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, whether male or female, are intended to be covered. A subject may also be afflicted with a disease or disorder. The term "patient" may be used to specifically refer to a subject afflicted with a disease or disorder. The term "patient" includes human and veterinary subjects.

As used herein, the term "diagnosed" means having been subjected to a physical examination by a person of skill, for example, a physician, and found to have a condition that can be diagnosed or treated by the compounds, compositions, or methods disclosed herein. Such a diagnosis can be in reference to a disorder, such as diabetes, and the like, as discussed herein.

Embodiments

In one embodiment, the present invention relates to a method of inducing production of full-length progranulin (GRN) from a nucleotide encoding a GRN with a premature stop codon (GRN-PTC), comprising exposing the GRN-PTC to an aminoglycoside. In other embodiments, the aminoglycoside is selected from gentamicin or G418. In some embodiments of the present invention, the premature stop codon is R493X. In a further embodiment of the present invention, the GRN nucleotide is in a cell. In some embodiments of the present invention, the aminoglycoside is administered to the cell at a concentration between about 100 μg/mL and 2000 μg/mL. In further embodiments of the present invention, the cell is a neuronal cell. In other embodiments, the cell is in a patient with frontotemporal dementia (FTD).

As used herein, the terms "administering," "administered," and "administration" refer to any method of providing an aminogycoside to a patient or cell. Such methods of administering to a patient are well known to those skilled in the art and include, but are not limited to, intraperitoneal injection, intravenous injection, or intraarterial injection. Other modes of administration include, for example, subcutaneous administration and intranasal administration.

In some embodiments of the presently-disclosed subject matter, the aminoglycoside can be administered at a dose of about 100 μg/mL. In some embodiments, the aminoglycoside can be administered at a dose of about 100, 500, 1002, or 2000, μg/mL. In some embodiments, the aminoglycoside can be administered for 6 hours, 12 hours, 24 hours, or 48 hours. In other embodiments the aminoglycoside can be administered for up to 48 hours.

EXAMPLES

Materials & Methods

Plasmids

The WT progranulin plasmid with a C-terminal FLAG tag (pC-Flag-PGRN-WT) was purchased from Sino Biological Inc. (Cat. HG10826-CF). Three nonsense mutations, Q125X, R229X and R493X, were generated using Q5 site-directed mutagenesis kit (New England Biolabs Inc., Cat. E0554S) to introduce a single nucleotide substitution in the WT progranulin gene (FIG. 1A). The WT progranulin with an N-terminal HA tag (HA-PGRN) was also generated by subcloning using the p3xHA vector (58) and HindIII and BamHI sites.

Antibodies

The primary antibodies for Western analysis and immunofluorescence microscopy were mouse anti-Flag (Sigma, F3165), rabbit anti-Actin (Cell Signaling Technology, Cat. 8457), mouse anti-Flag (Sigma, A8592), rabbit anti-PGRN (Novus, NAP1-87324), goat anti-PGRN (R&D, AF2420), sheep anti-progranulin (R&D, AF2557-SP), rabbit anti-HA (Santa Cruz, sc-805), mouse anti-HA (Santa Cruz, sc-7392), rabbit anti-Lamp1 (Cell Signaling Technology, 9091S), goat anti-Lamp1 (R&D, AF4320), rabbit anti-GM130 (Cell Signaling Technology, 12480P) and rabbit anti GM130 (Novus, NBP2-53420SS). The secondary antibodies were Alexa Fluor 488 donkey anti-mouse (Life Technologies, A-21202), Alexa Fluor 568 donkey anti-rabbit (Life Technologies, A-10042), and Alexa Fluor 568 donkey anti-goat (Life Technologies, A-11057).

Cell Culture, Transfection and Drug Treatment

N2A cells were maintained in DMEM (Sigma, D5796) supplemented with 10% fetal bovine serum, 100 unit/mL penicillin, and 100 μg/mL streptomycin. Transient transfection was performed using Lipofectamine 2000 (Invitrogen, Life Technologies, Grand Island, N.Y., USA). 2 of total plasmid was used for each well of 6-well plate unless otherwise described. After 6 hours transfection, fresh medium containing aminoglycoside at indicated concentrations was added to cells. Cells were applied to following experiments after exposed to drugs at certain time points. All cells were kept in a humidified incubator at 37° C. under 5% $CO_2$/95% air.

Eleven aminoglycosides were tested in this study: G418 (Sigma-Aldrich, Cat. 4727878001), gentamicin (Sigma-Aldrich, Cat. G1397), Kanamycin (Gold Biotechnology, Cat. K-120-25), Streptomycin (Sigma-Aldrich, Cat. S9137), Amikacin (Alta Aesar, Cat. J67496), Tobramycin (Alta Aesar, Cat. J62995), Apramycin (Sigma-Aldrich, Cat. A2024), Neomycin B (Sigma-Aldrich, Cat. N6386), Netilmicin (Alta Aesar, Cat. J66302), Paromomycin (Alta Aesar, Cat. J61274), Sisomicin (Sigma-Aldrich, Cat. S7796). PTC124 was purchased from Med Chem Express (Cat. 775304-57-9).

Western Blots

Cells were lysed in RIPA buffer (Millipore Sigma, Cat. 20-188), centrifuged at 1000 g for 10 mins to remove debris, and then subjected to SDS electrophoresis. After electrophoresis, gels were proceeded for transferring onto nitrocellulose membranes. The membranes were then blocked with 5% milk in TBST (100 mM TRIS-HCl, pH7.5, 0.9% NaCl, 0.1% Tween-20) and incubated with indicated primary antibodies in the same solution. All immunoblotting images were acquired using a BioRad ChemiDoc MP system.

Immunofluorescence Microscopy

Cells were seeded on gelatin coated glass coverslips and transfected with progranulin constructs. Twenty-four hours later with or without drug treatments, cells were rinsed with 1×PBS, fixed with 4% formaldehyde in 1×PBS, and permeabilized with 0.25% Triton-X100 in 1×PBS. The samples were mounted by applying Vectashield Mounting Medium (Vector Laboratories) and visualized using a Nikon A1 confocal microscope with a 60× objective. Mander's overlap coefficients (MOE) were calculated using NIS-Elements AR (Nikon, v3.2, 64 bit) to assess protein colocalization.

Quantitative PCR

Total RNA was extracted with Aurum total RNA mini kit (BioRad, Cat. 732-6820), and cDNA was generated with SuperScript III first-strand synthesis system for RT-PCR (Invitrogen, Cat. 18080-051). Quantitive PCR was performed using SYBR Green (ThermoScientific, Cat. 4309155). Beta-actin primers: forward 5'-AGA GCT ATG AGC TGC CTG AC-3' (SEQ ID NO: 1); reverse 5'-GGA TGT CAA CGT CAC ACT TC-3'(SEQ ID NO: 2). Primers used for full length progranulin mRNA (including flag encoding sequence) is: forward 5'-CGT GAA GGC TTG ATC CTG CGA GA-3' (SEQ ID NO: 3), reverse 5'-CTT ATC GTC ATC CTT GTA ATC-3' (SEQ ID NO: 4). Annealing temperature for both beta-actin and progranulin qPCR reaction were 60° C.

Example 1. G418 and gentamicin induce read-through of the progranulin R493X nonsense mutation.

WT progranulin and three plasmids each with a single nonsense mutation (Q125X, Y229X, or R493X) and a C-terminal Flag tag (FIG. 1A) were constructed. A full-length protein must be generated for the FLAG to be detected, thus a truncated progranulin will not be detected by FLAG Western blotting. If read-through of the progranulin PTC occurs, then progranulin will be detectable by FLAG Western blotting.

R493X, which is the most common nonsense mutation in progranulin-mediated familial FTD (8, 31), was chosen to test whether aminoglycosides could induce read-through. N2A cells were transfected with the indicated plasmid, allowed to recover for 6 hours, and fresh media containing the aminoglycoside at the indicated concentrations was added to the cells for 24 hours. Cells were lysed and analyzed by Western blotting to determine the amount of progranulin protein. Among eleven commercially available aminoglycosides and PTC124, only gentamicin and G418 induced read-through of R493X as evidenced by positive bands in FLAG Western blot (FIG. 1B). The other nine aminoglycosides (kanamycin, streptomycin, amikacin, tobramycin, apramycin, neomycin B, netilmicin, paromomycin and sisomicin) and PTC124 did not have any detectable read-through effect as no FLAG-positive bands were observed. No signal was detected in lysate from cells transfected with R493X in the absence of any compounds, serving as a negative control. The FLAG-tagged WT progranulin was included as a positive control to define the expected progranulin-FLAG amount. In addition, Western analysis using a progranulin antibody that detects full-length protein and the R493X protein also demonstrated the expression of full-length progranulin from R493X plasmid in the presence of gentamicin or G418 (FIG. 1B). It is noted that G418 induced a stronger effect than gentamicin.

Figure 6A:
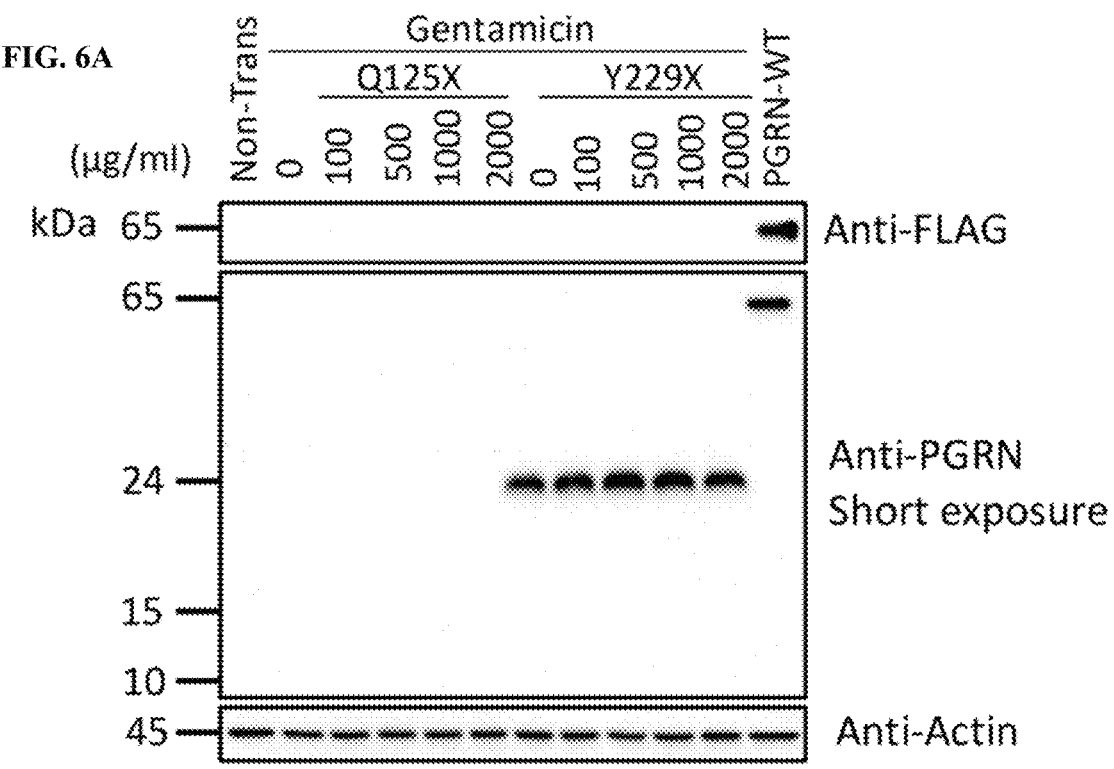
FIG. 6A shows Gentamicin did not induce readthrough of progranulin PTC mutations Q125X or Y229X or FUS PTC mutation R495X. Gentamicin had no readthrough effect on two other FTD mutations Q125X and Y229X. N2A cells were transfected with Q125X or Y229X proganulin, allowed to recover, and treated with two different concentrations of each compound for 24 hours. Cell lysates were generated, separated by SDS-PAGE, and analyzed by Western analysis using anti-FLAG (top), anti-progranulin (middle), and anti-actin (lower) antibodies. In the anti-progranulin blot, the higher band is WT progranulin and the lower band is the Q229Y truncated protein.
Figure 6B:
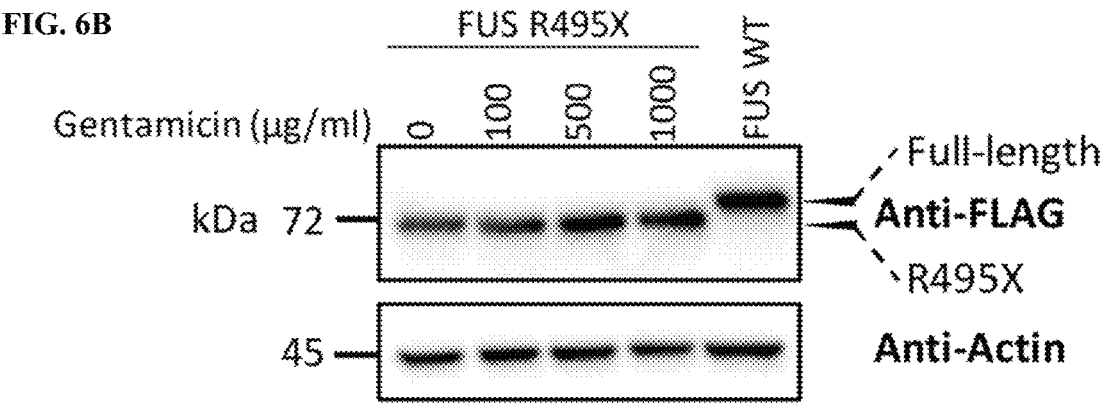
FIG. 6B shows Gentamicin did not induce readthrough of progranulin PTC mutations Q125X or Y229X or FUS PTC mutation R495X. Gentamincin had no readthrough effect on the FUS R495X mutation responsible for familial ALS. N2A cells were transfected with WT or R495X FUS, allowed to recover, and treated with three concentrations of G418 for 24 hours. Cells were harvested and cell lysates were subjected to SDS-PAGE and Western analysis using anti-FLAG (top) and anti-actin (lower) antibodies. The slightly higher band is full-length WT FUS and the lower band is R495X truncated FUS. Gentamicin did not induce readthrough of R495X FUS.

Whether G418 or gentamicin could induce read-through of two additional progranulin nonsense mutations (Q125X or Y229X) and a FUS nonsense mutation R495X that has been identified in juvenile patients of the related neurodegenerative disease ALS was also tested. Interestingly, G418 did not have any read-through effect on the progranulin Q125X or Y229X mutation as no full-length read-through protein was detected by the FLAG antibody (FIG. 1C). G418 did not induce read-through of the FUS R495X mutation either since the full-length protein was not observed (FIG. 1D). Similarly, gentamicin did not induce read-through of Q125X, Y229X, or R495X either (FIG. 6A-6B). The above data collectively support that G418 and gentamicin specifically induced read-through of the progranulin R493X mutation.

Example 2. G418 and gentamicin induce the read-through of progranulin R493X in a dose- and time-dependent manner.

Figure 2B:
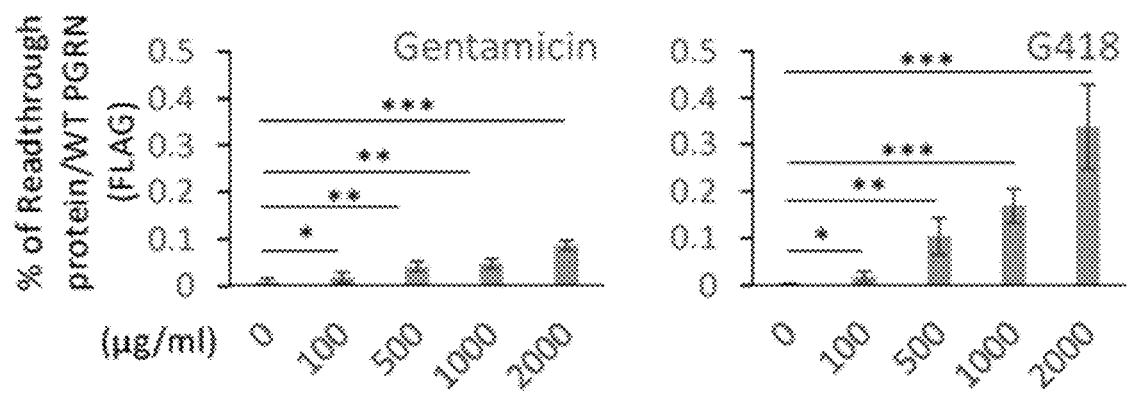
FIG. 2B shows G418 and gentamicin induced dose-dependent R493X progranulin readthrough. Band intensities were quantified to determine the dose response of readthrough efficiency. All FLAG bands were normalized against corresponding actin bands and the individual readthrough band was subsequently compared to the WT progranulin (the last lane in FIG. 2A). *, $p<0.1$; , $p<0.01$; *, $p<0.001$.

A series of G418 and gentamicin concentrations were tested to examine the dose response of the read-through effect. N2A cells were transfected with the R493X progranulin plasmid, allowed to recover for 6 hours, fresh media containing either G418 or gentamicin at 100, 500, 1000 or 2000 μg/ml was added to cells for 24 hours. Cells were then lysed and lysates analyzed by Western blotting. The read-through was dose-dependent with the highest progranulin-FLAG signal corresponding to the highest concentration of compound (FIG. 2A). Band intensity of the FLAG-tagged read-through proteins were quantified as a percentage of the WT progranulin (the last lane in FIG. 2A). A maximum read-through of 33.8% was observed when cells expressing R493X progranulin were treated with 2000 μg/ml of G418 (FIG. 2B). While G418 yielded >30% read-through, the maximal concentration of gentamicin produced 8.6% read-through.

Figure 3A:
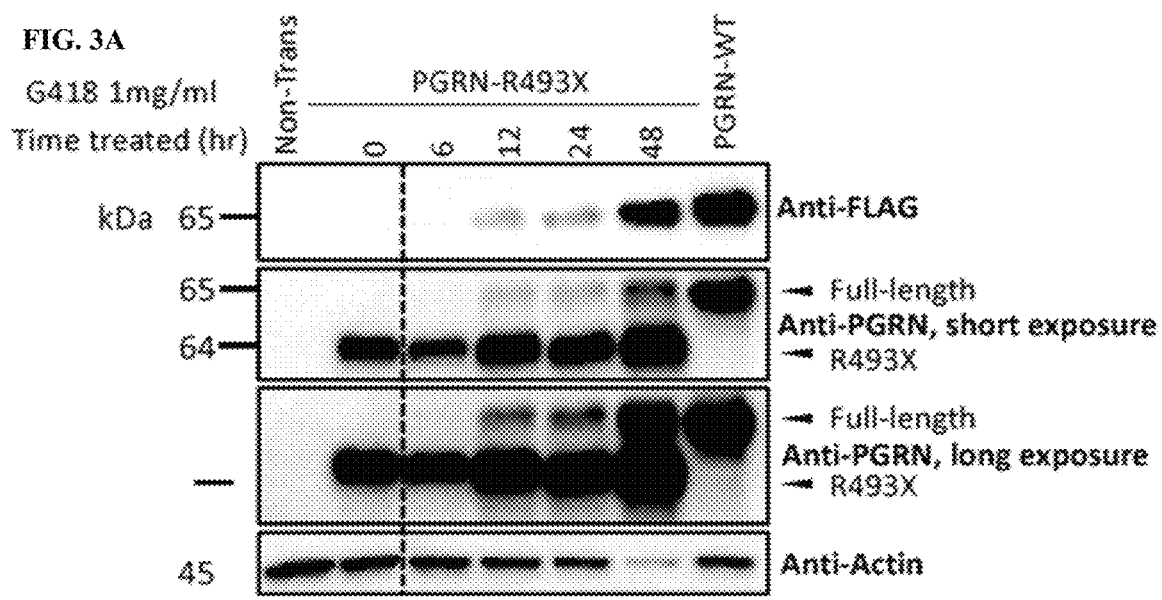
FIG. 3A shows Time dependent readthrough effect by gentamicin and G418 on progranulin R493X. G418 induced readthrough of R493X mutation of progranulin in a time-dependent manner. Cells were treated as in FIG. 1A-D and lysates analyzed by Western analysis using an anti-FLAG (top blot), anti-progranulin (middle blots), and anti-actin (lower blot) antibodies. The two middle blots are a short and long exposure of the anti-progranulin analysis.
Figure 3B:
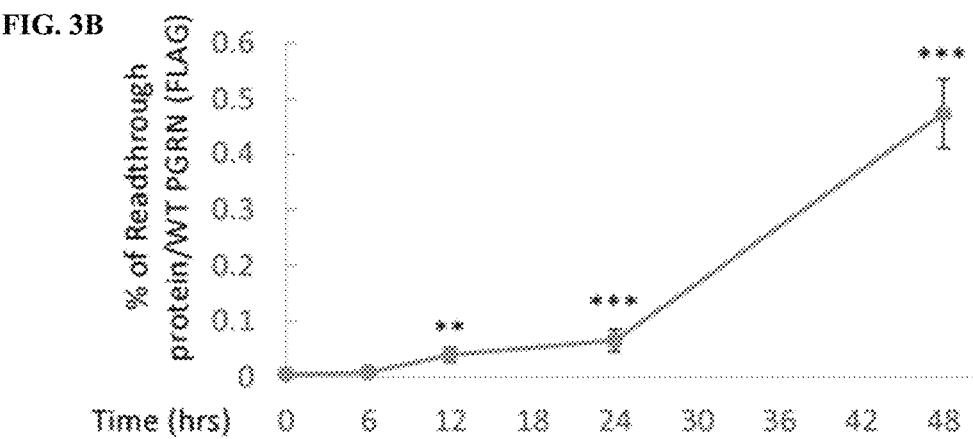
FIG. 3B shows Time dependent readthrough effect by gentamicin and G418 on progranulin R493X. Band intensities were quantified to determine readthrough efficiency of the time-course. All FLAG bands were normalized against corresponding actin bands and the individual readthrough band was compared to the WT progranulin (the last lane in A). , $p<0.01$; *, $p<0.001$.
Figure 3C:
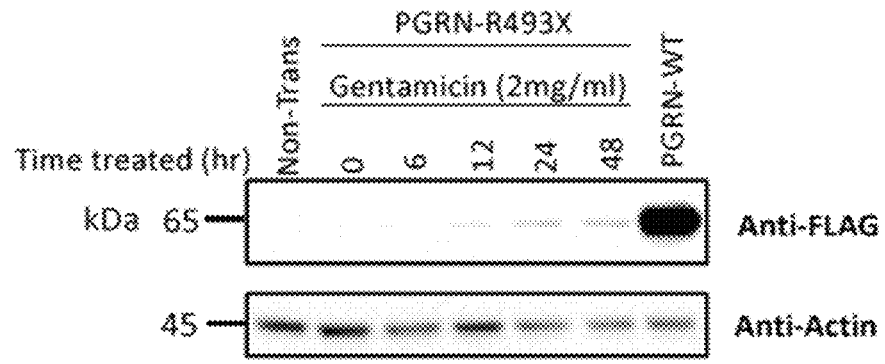
FIG. 3C shows Time dependent readthrough effect by gentamicin and G418 on progranulin R493X. The time-course of gentamicin-induced readthrough effect on R493X.

Example 3. Next the read-through effect of G418 and gentamicin were examined with respect to time. In this experiment, 1000 μg/ml of G418 or 2000 μg/ml of gentamicin was added to cells for the indicated number of hours before cells were harvested for analysis. Readthrough of full-length progranulin was detected by both FLAG and the progranulin antibody after 12 hours of G418 treatment. After 12 hours of G418 treatment, the read-through was ≈5% of the WT control and it increased up to 47.3% after 48 hours (FIGS. 3A-B). Treatment with gentamicin yielded a similar time-dependent read-through though the maximum read-through was less than 10% (FIG. 3C).

Example 4. G418-induced read-through protein displays similar subcellular localization as WT progranulin.

Figure 4A:
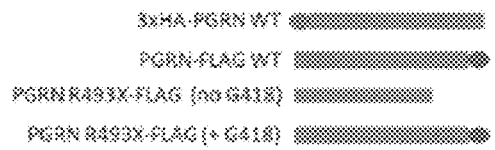
FIG. 4A shows Subcellular localization of the G418-induced R493X readthrough and WT progranulin. A schematic of N- and C-terminal tagged WT progranulin and expected proteins in the absence and presence of G418. All G418 treatment was 1000 µg/ml for 24 hours in this figure.
Figure 4B:
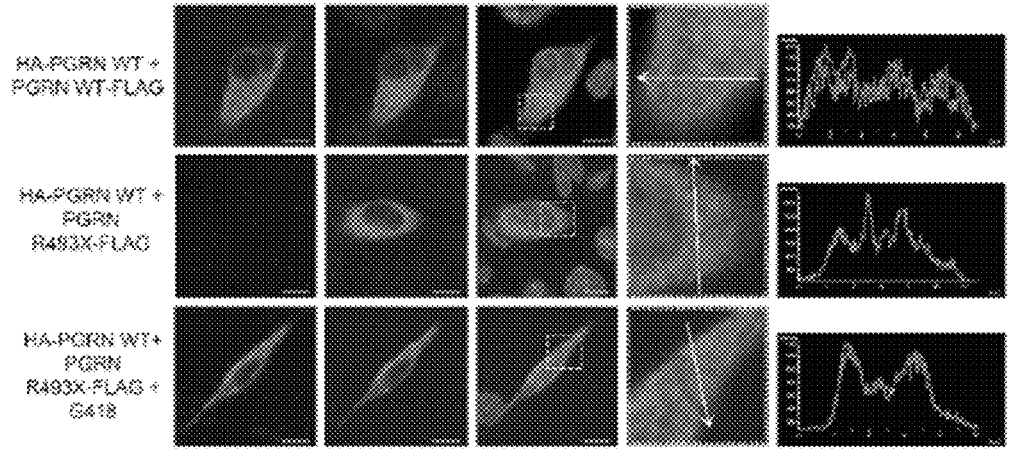
FIG. 4B shows Subcellular localization of the G418-induced R493X readthrough and WT progranulin. Top: The N-terminal HA-tagged and C-terminal FLAG-tagged WT progranulin are largely co-localized in N2A cells. Middle: N2A cells expressing HA-tagged WT progranulin and FLAG-tagged R493X-progranulin in the absence of G418. No FLAG signal was observed in the absence of G418. Bottom: N2A cells expressing HA-tagged WT progranulin and FLAG-tagged R493X-progranulin in the presence of G418. The FLAG-tagged R493X readthrough protein co-localizes with the HA-tagged WT progranulin. A histogram shows green (FLAG) and red (HA) signals along the cross section line drawn in the zoom view for each row. The concurrence of green and red signals demonstrates the co-localization of FLAG- and HA-tagged proteins.

Aminoglycoside-induced read-through is predicted to introduce a near-cognate amino acid into the PTC site (32), thus it is necessary to evaluate whether the read-through protein exhibits similar function as WT progranulin. Since the function of progranulin is complex and there is no established progranulin activity assay, the subcellular localization of the read-through progranulin was examined to determine if it is similar as WT. Both N-terminal HA-tagged and C-terminal FLAG-tagged progranulin plasmids were co-transfected (FIG. 4A) into N2A cells and determined their subcellular localization using immunofluorescence microscopy. Confocal images demonstrate that the HA-tagged and FLAG-tagged WT progranulin were largely co-localized (FIG. 4B, top row). Analysis using NIS-Elements AR software (Nikon, v3.2) demonstrates a Mander's overlap coefficient (MOC) of 0.94, meaning the sum of the intensities of red pixels that also have green component divided by the total sum of red intensities is 94% (33). Conversely, when HA-WT progranulin was co-expressed with R493X-progranulin-FLAG in the absence of G418, there was no FLAG staining (FIG. 4B, middle row). Strikingly, the read-through protein of R493X-progranulin-FLAG in the presence of G418 yielded robust FLAG signal that co-localized with HA-tagged WT progranulin (FIG. 4B, bottom row). The degree of co-localization as assessed by MOC is 0.97, comparable to that of the WT controls.

Figure 4C:
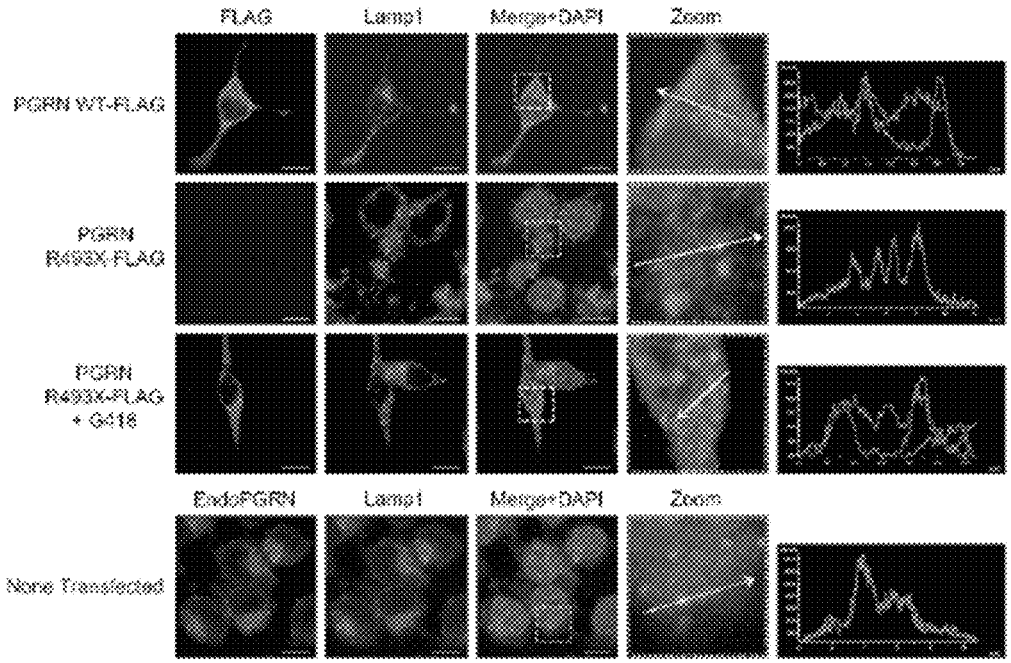
FIG. 4C shows Subcellular localization of the G418-induced R493X readthrough and WT progranulin. The overexpressed WT progranulin (top), the G418-induced readthrough full-length protein (third row), and the endogenous progranulin (bottom) are partially co-localized with lysosome marker Lamp1. No FLAG signal was observed in the absence of G418 (second row).
Figure 4D:
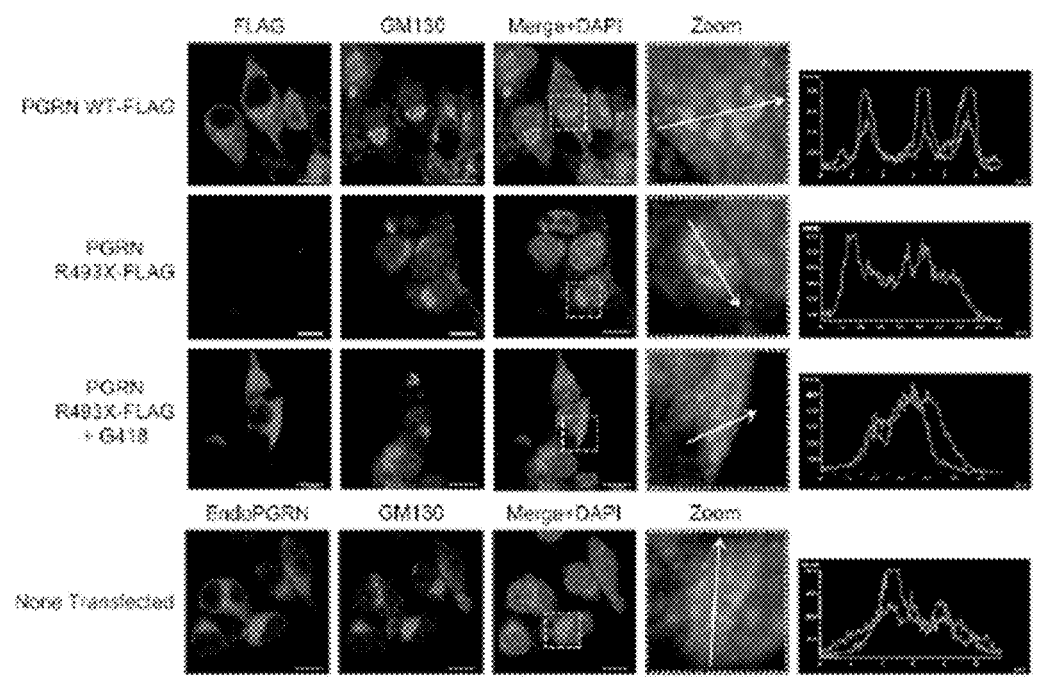
FIG. 4D shows Subcellular localization of the G418-induced R493X readthrough and WT progranulin. The overexpressed WT progranulin (top), the G418-induced readthrough full-length protein (third row), and the endogenous progranulin (bottom) are partially co-localized with Golgi marker GM130. No FLAG signal was observed in the absence of G418 (second row). Scale bars, 20 µm.

Progranulin is reported to play a role in endocytosis, secretion, and lysosomal pathways (34). Therefore, the co-localization of R493X-progranulin read-through protein with the lysosome marker Lamp1 was examined. Transiently expressed WT progranulin (FIG. 4C, top row, MOC of 0.59) and the G418-induced R493X-progranulin read-through protein (FIG. 4C, third row, MOC of 0.67) shared a similar pattern, i.e. both were partially co-localized with Lamp1. As a positive control, endogenous progranulin was examined in N2A cells and observed to largely co-localize with Lamp1 (FIG. 4C, bottom row, MOC of 0.97). There was no FLAG signal from cells transfected with R493X-progranulin in the absence of G418 (FIG. 4C, second row), serving as a negative control. Similarly, WT progranulin (FIG. 4D, top row, MOC of 0.63) and the G418-induced R493X read-through protein (FIG. 4D, third row, MOC of 0.53) were partially co-localized with the Golgi apparatus marker GM130. As a positive control, the endogenous progranulin was also partially co-localized with GM130 (FIG. 4D, bottom row, MOC of 0.87). As a negative control, there was no FLAG signal in the absence of G418 (FIG. 4D, second row). These results demonstrate that the G418-induced read-through protein shared a similar sub-cellular localization as the overexpressed WT progranulin in N2A cells, i.e. partial co-localization with lysosomal and Golgi markers. The endogenous progranulin showed a higher degree of co-localization with Lamp1 and GM130. The results suggest that the induced read-through protein possesses a similar function as WT progranulin.

Example 5. G418 treatment stabilizes full-length progranulin mRNA in cells.

In addition to inducing read-through, it has been reported that aminoglycosides can also stabilize mRNAs, which could enhance the read-through effect (35, 36). Therefore, qPCR was used to determine the mRNA levels in the absence and presence of G418. First, a significant decrease of the full-length mRNA containing R493X PTC mutation was observed as compared to WT progranulin, indicating that the R493X mutant mRNA was turned over more rapidly. In the presence of different doses of G418, the full-length mRNA containing R493X mutation increased up to two-fold as compared to that in the absence of G418 (FIG. 5), suggesting that G418 indeed stabilized R493X mutant mRNA. These results indicate that the higher level of full-length progranulin mRNA in G418 treated cells may also contribute to the G418-induced read-through.

Figure 7:
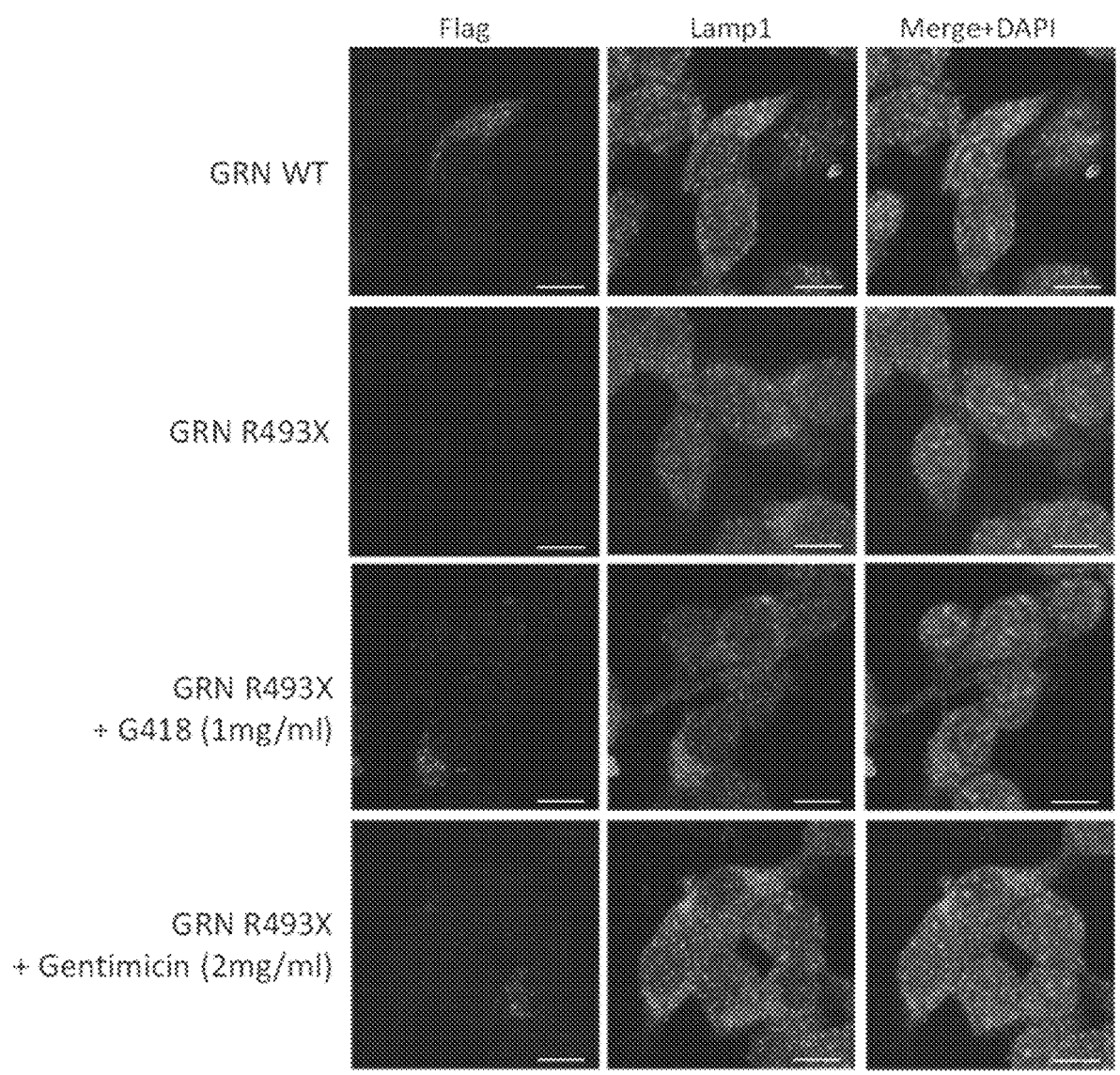
FIG. 7. Shows the colocalization of progranulin with the lysosome marker Lamp1. Top row: wild-type progranulin, 2nd row: R493X without G418 or gentamicin. 3rd row: R493A after 24 hours treatment of G418. Bottom row: R493A after 24 hours treatment of gentamicin.

Example 6. Induced read-through protein shares the lysosome localization as wild-type progranulin. The subcellular localization of wild-type and R493X read-through protein in N2A cells were examined using confocal microscopy (FIG. 7). The wild-type progranulin (FLAG staining) was co-localized with the lysosome marker Lamp1 (top row). The R493X plasmid produced little FLAG staining signals in the absence of gentamicin or G418 (second row). In the presence of G418 (third row) or gentamicin (bottom row), the induced read-through protein (FLAG staining) was also co-localized with Lamp1. These results together support that the induced read-through protein shared the same sub-cellular localization as wild-type progranulin.

Discussion

To determine whether aminoglycosides can induce read-through of nonsense mutations in progranulin and FUS, two genes implicated in two related neurodegenerative diseases. R493X, Y229X and Q125X mutations in progranulin have been reported in familial FTD. R495X mutation has been found in juvenile familial ALS patients (37). Among 12 compounds tested (11 aminoglycosides and PTC124), two aminoglycosides, G418 and gentamicin, were identified that specifically induced the read-through of R493X progranulin (FIG. 1B) in a dose- and time-dependent manner (FIGS. 2A-B, 3A-C). G418 displayed dramatically better efficacy than gentamicin with respect to both time and dose. Importantly, the induced read-through protein shared similar lysosome and Golgi apparatus localization as the WT progranulin (FIGS. 4A-D).

Among 14 nonsense progranulin mutations reported to be associated with FTD, R493X is the most frequent, accounting for ~20% of progranulin-mediated FTD cases (8, 31, 38). In contrast, Q125X and Y229X are rare (39, 40). ALS and FTD are highly related as they share a wide spectrum of clinical, pathological and genetic features (41), thus a FUS nonsense mutation implicated in ALS was included in this study. FUS R495X is a particularly severe mutation that leads to clinical manifestation in juvenile ALS patients (37). Among the four PTCs tested, read-through was observed only for progranulin 493X upon G418 or gentamicin treatment whereas no read-through was detected for Q125X or Y229X progranulin or R495X FUS (FIGS. 1A-D). Previous studies have demonstrated that read-through is mainly influenced by two factors: the nucleotide sequence of the PTC and the flanking nucleotides (42, 43). It is reported that the difficulty of reading-through a PTC increases from TGA to TAG to TAA (44). In addition, better read-through efficiency was observed with a C or T at the upstream −1 position and C at the downstream +4 position (42). The sequences of these four nonsense mutations are compiled in Table 1. The R493X mutation in human FTD patients has TGA as a PTC along with T at both upstream −1 nt and downstream +4 nt positions (Table 1). Other than the sites −1 to +4 (bolded), all other bases may be mutated in the population with a frequency expected by one of ordinary skill in the art.

TABLE 1

PTC and flanking sequences of the nonsense mutations.

| | WT sequence | PTC sequence | Flanking sequence |
|---|---|---|---|
| | | | −1     +4 |
| R493X progranulin | CGA | TGA | CGTGAAGGCTTGATCCTGCGAGA (SEQ ID NO: 5) |
| Y229X progranulin | TAT | TAA | CAGTGGGAAGTAAGGCTGCTGCC (SEQ ID NO: 6) |
| Q125X progranulin | CAG | TAG | GGGTGCCATCTAGTGCCCTGATA (SEQ ID NO: 7) |
| R495X FUS | CGA | TGA | TGGAGGCTTCTAGGGGGGCCGGG (SEQ ID NO: 8) |
| Favorable factors | | TGA > TAG > TAA | C or T @−1 C @+4 |

The combination of a favorable TGA PTC and a T at the −1 position are possible reasons that G418 and gentamicin induced R493X read-through. The PTC for Y229X is TAA, which is the most difficult stop codon for read-through. Indeed, read-through product from progranulin Y229X by either G418 or gentamicin was observed. The PTC for Q125X is TAG and the flanking sequence is C at the −1 and T at +4 position, respectively. The TAG PTC is less optimal, C at −1 position is favorable but T at +4 position is less favorable. Consequently no read-through was observed for Q125X. Similarly in the case of R495X FUS, the TAG PTC is less favorable, C at −1 position is favorable, and G at +4 position is less favorable. These are likely factors explaining no detectable read-through for R495X FUS.

G418 exhibited higher efficacy (~47.3% after 48 hours) on progranulin R493X mutation than gentamicin (no more than 10%) (FIGS. 1B, 2A-B and 3A-C). The nearly 50% read-through efficiency of R493X by G418 was better than the reported ~10% read-through of the dystrophin PTC by G418 (23) and ~20-35% read-through of the CFTR PTC by G418 (21, 22), and comparable to ~30-50% read-through of the LAMB3 PTC by gentamicin (27). Conversely, nine other aminoglycosides or PTC124 showed no detectable effect (FIG. 1B). It is suggested that the interactions of aminoglycosides with 80S eukaryotic ribosomes are critical for the read-through effect. Aminoglycoside-ribosome interactions allows errors in tRNA selection and consequentially leads to the read-through of PTCs. (20). Among 12 compounds tested (eleven different aminoglycosides and PTC124), only gentamicin and G418 showed read-through effect. It is likely that the structure of these aminoglyucosides differ in a way to affect their binding modes to eukaryotic ribosomes, thus producing different read-through efficiency. It is noted that PTC124 is not an aminoglycoside but has similar effect on ribosome to induce read-through of PTCs (46). PTC124 is the only read-through compound approved clinically to treat DMD in Europe (47). However PTC124 did not have any detectable effect on R493X progranulin. The results provide initial insights into the structure-activity relationship and will help future studies to design and develop novel compounds with better efficacy and specificity.

The aminoglycoside-induced read-through inserts a near-cognate amino acid at the PTC position. It was reported that Gln, Tyr or Lys was inserted at UAA and UAG and that Trp, Arg or Cys was inserted at UGA (32). The frequency of insertion of individual amino acid was distinct for specific PTC codons and read-through-inducing agents (32). Because of the unknown amino acid at the R493 position, it was necessary to examine whether the read-through protein functions the same as WT progranulin.

Multiple studies reported that progranulin plays a role in lysosome (19, 48, 49). It has been reported to regulate the maturation of lysosomal hydrolases (50) and homozygous progranulin mutation leads to a lysosomal storage disease NCL (15, 51). In addition, progranulin itself is processed into granulin peptides (52, 53). Progranulin has been reported to be partially co-localized with lysosome markers in multiple studies (18, 52). Indeed, both endogenous and overexpressed WT progranulin co-localized with lysosome marker Lamp1 (FIG. 4C). More importantly, the G418-induced read-through protein from R493X was also partially co-localized with Lamp1, in a similar fashion as WT progranulin (FIG. 4C). In addition, the R493X read-through protein shared a similar pattern with WT progranulin as both were partially co-localized with the Golgi apparatus marker GM130 (FIG. 4D). It is necessary to place an epitope tag at the C-terminus of the R493X mutant to allow specific detection of the G418-induced read-through protein in confocal imaging studies as evidenced by the lack of FLAG signals in the absence of G418 (FIGS. 4B-4D). Progranulin can be targeted to lysosomes by two independent mechanisms that are mediated by sortilin (34) and prosaposin (54, 55), respectively. It is noted that the C-terminal tagging may interfere with the sortilin-dependent trafficking since its C-terminus is critical to its interaction with sortilin (56). The partial co-localization of the FLAG-tagged WT progranulin and G418-induced read-through protein with the lysosomal marker Lamp1 (FIG. 4C) is consistent with the previous studies. More importantly, the subcellular localization of the G418-induced read-through protein is highly similar to that of WT progranulin (FIGS. 4A-D). Thus, G418-induced read-through protein likely functions similarly as WT progranulin.

Figure 5:
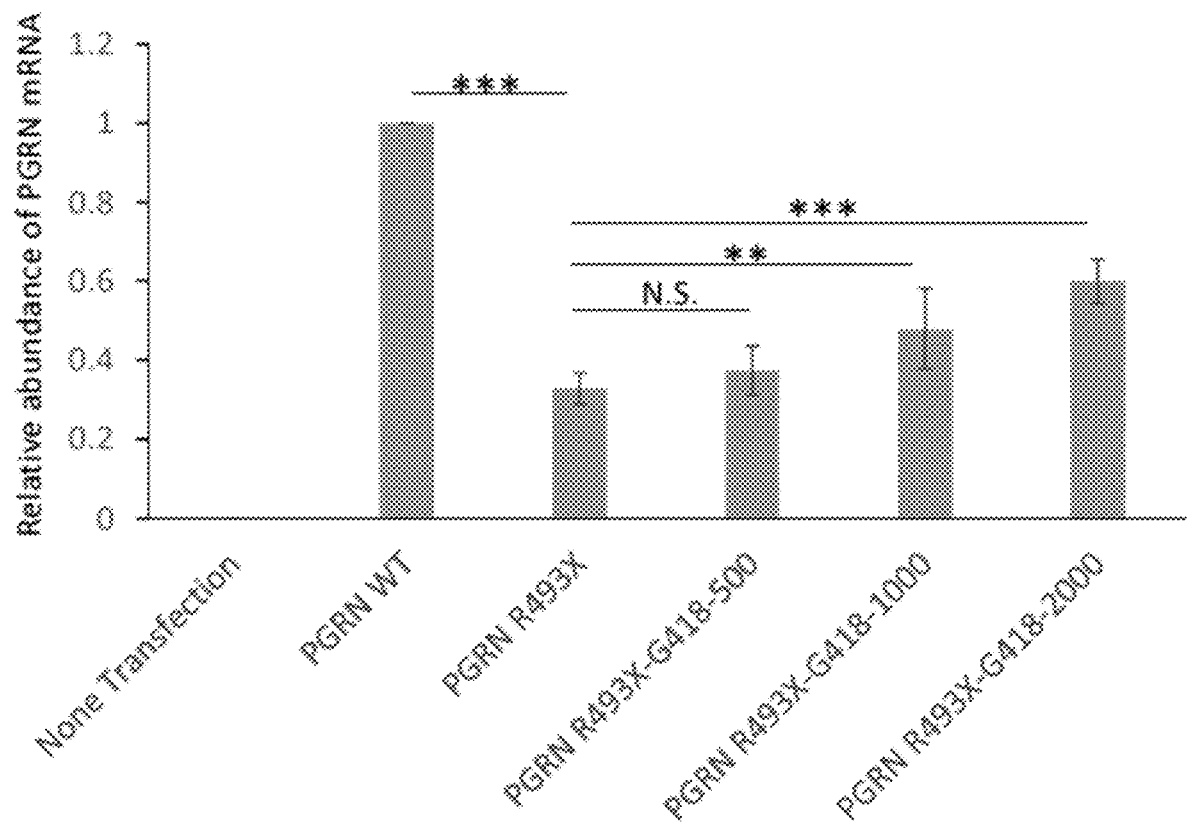
FIG. 5 shows mRNAs levels of WT and R493X progranulin in the absence and presence of G418. N2A cells were exposed to G418 treatment for 24 hours with indicated concentrations after transfection. Primers specific for full length PGRN mRNA were used for qPCR. All results were normalized to full length WT progranulin in non-treated cells. N.S.: no significance. , p<0.01; *, p<0.001.

In addition to the read-through effect, G418 could also stabilize mRNA by antagonizing nonsense-mediated decay (NMD) in mammalian cells (22, 35, 36). Treatment with G418 treatment increased the level of Xeroderma pigmentosum complementation group C (XPC) mRNA containing nonsense mutations to about 20%-70% of normal level, which exerts a smaller but similar effect as NMD inhibitor cycloheximade (57). It is further notable that the mRNA level of R493X increased from ~30% of WT progranulin in the absence of G418 to ~60% with G418 treatment (FIG. 5). The binding of G418 to the eukaryotic ribosome, which triggers the translation machinery to continue translation until the real stop codon is reached, may be an effective way to avoid the activation of NMD. While the absence of NMD activation would in turn make it possible for cells to maintain a higher level of PTC-containing mRNA, leading to a higher efficiency in read-through. It is noted that both mechanisms can be leveraged in future translational studies.

In summary, the present invention is directed towards gentamicin and G418 inducing read-through of the progranulin 493X mutation to produce full-length progranulin protein in an in vitro cell culture model.

It will be understood that various details of the presently disclosed subject matter can be changed without departing from the scope of the subject matter disclosed herein. Furthermore, the foregoing description is for the purpose of illustration only, and not for the purpose of limitation.

SEQUENCE LISTING

In accordance with 37 C.F.R § 1.821 and MPEP 2422.03, a sequence listing was submitted via EFS-web. The sequence listing, an ASCII text file entitled "13177N_2295US Sequence Listing.txt" created on Dec. 17, 2019, and having a file size of 1,742 bytes, is herein incorporated by this reference in its entirety.

REFERENCES

Each of the following references is herein incorporated by reference in their entirety.

1 Snowden, J. S., Pickering-Brown, S. M., Mackenzie, I. R., Richardson, A. M., Varma, A., Neary, D. and Mann, D. M. (2006) Progranulin gene mutations associated with frontotemporal dementia and progressive non-fluent aphasia. *Brain*, 129, 3091-3102.
2 Van Langenhove, T., van der Zee, J. and Van Broeckhoven, C. (2012) The molecular basis of the frontotemporal lobar degeneration-amyotrophic lateral sclerosis spectrum. *Annals of medicine*, 44, 817-828.
3 Baker, M., Mackenzie, I. R., Pickering-Brown, S. M., Gass, J., Rademakers, R., Lindholm, C., Snowden, J., Adamson, J., Sadovnick, A. D., Rollinson, S. et al. (2006) Mutations in progranulin cause tau-negative frontotemporal dementia linked to chromosome 17. *Nature*, 442, 916-919.
4 Rohrer, J. D., Guerreiro, R., Vandrovcova, J., Uphill, J., Reiman, D., Beck, J., Isaacs, A. M., Authier, A., Ferrari, R., Fox, N. C. et al. (2009) The heritability and genetics of frontotemporal lobar degeneration. *Neurology*, 73, 1451-1456.

5 Pottier, C., Ren, Y., Perkerson, R. B., 3rd, Baker, M., Jenkins, G. D., van Blitterswijk, M., DeJesus-Hernandez, M., van Rooij, J. G. J., Murray, M. E., Christopher, E. et al. (2019) Genome-wide analyses as part of the international FTLD-TDP whole-genome sequencing consortium reveals novel disease risk factors and increases support for immune dysfunction in FTLD. *Acta Neuropathol*, 137, 879-899.

6 Mackenzie, I. R., Neumann, M., Baborie, A., Sampathu, D. M., Du Plessis, D., Jaros, E., Perry, R. H., Trojanowski, J. Q., Mann, D. M. and Lee, V. M. (2011) A harmonized classification system for FTLD-TDP pathology. *Acta Neuropathol*, 122, 111-113.

7 Cruts, M., Gijselinck, I., van der Zee, J., Engelborghs, S., Wils, H., Pirici, D., Rademakers, R., Vandenberghe, R., Dermaut, B., Martin, J. J. et al. (2006) Null mutations in progranulin cause ubiquitin-positive frontotemporal dementia linked to chromosome 17q21. *Nature*, 442, 920-924.

8 Gass, J., Cannon, A., Mackenzie, I. R., Boeve, B., Baker, M., Adamson, J., Crook, R., Melquist, S., Kuntz, K., Petersen, R. et al. (2006) Mutations in progranulin are a major cause of ubiquitin-positive frontotemporal lobar degeneration. *Hum Mol Genet*, 15, 2988-3001.

9 Chitramuthu, B. P., Bennett, H. P. J. and Bateman, A. (2017) Progranulin: a new avenue towards the understanding and treatment of neurodegenerative disease. *Brain*, 140, 3081-3104.

10 He, Z., Ong, C. H., Halper, J. and Bateman, A. (2003) Progranulin is a mediator of the wound response. *Nat Med*, 9, 225-229.

11 Ahmed, Z., Mackenzie, I. R., Hutton, M. L. and Dickson, D. W. (2007) Progranulin in frontotemporal lobar degeneration and neuroinflammation. *J Neuroinflammation*, 4, 7.

12 Lui, H., Zhang, J., Makinson, S. R., Cahill, M. K., Kelley, K. W., Huang, H. Y., Shang, Y., Oldham, M. C., Martens, L. H., Gao, F. et al. (2016) Progranulin Deficiency Promotes Circuit-Specific Synaptic Pruning by Microglia via Complement Activation. *Cell*, 165, 921-935.

13 Martens, L. H., Zhang, J., Barmada, S. J., Zhou, P., Kamiya, S., Sun, B., Min, S. W., Gan, L., Finkbeiner, S., Huang, E. J. et al. (2012) Progranulin deficiency promotes neuroinflammation and neuron loss following toxin-induced injury. *J Clin Invest*, 122, 3955-3959.

14 Ryan, C. L., Baranowski, D. C., Chitramuthu, B. P., Malik, S., Li, Z., Cao, M., Minotti, S., Durham, H. D., Kay, D. G., Shaw, C. A. et al. (2009) Progranulin is expressed within motor neurons and promotes neuronal cell survival. *BMC Neurosci*, 10, 130.

15 Paushter, D. H., Du, H., Feng, T. and Hu, F. (2018) The lysosomal function of progranulin, a guardian against neurodegeneration. *Acta Neuropathol*, 136, 1-17.

16 Kao, A. W., McKay, A., Singh, P. P., Brunet, A. and Huang, E. J. (2017) Progranulin, lysosomal regulation and neurodegenerative disease. *Nat Rev Neurosci*, 18, 325-333.

17 Filiano, A. J., Martens, L. H., Young, A. H., Warmus, B. A., Zhou, P., Diaz-Ramirez, G., Jiao, J., Zhang, Z., Huang, E. J., Gao, F. B. et al. (2013) Dissociation of frontotemporal dementia-related deficits and neuroinflammation in progranulin haploinsufficient mice. *J Neurosci*, 33, 5352-5361.

18 Nguyen, A. D., Nguyen, T. A., Zhang, J., Devireddy, S., Zhou, P., Karydas, A. M., Xu, X., Miller, B. L., Rigo, F., Ferguson, S. M. et al. (2018) Murine knockin model for progranulin-deficient frontotemporal dementia with non-sense-mediated mRNA decay. *Proc Natl Acad Sci USA*, 115, E2849-E2858.

19 Arrant, A. E., Onyilo, V. C., Unger, D. E. and Roberson, E. D. (2018) Progranulin Gene Therapy Improves Lysosomal Dysfunction and Microglial Pathology Associated with Frontotemporal Dementia and Neuronal Ceroid Lipofuscinosis. *J Neurosci*, 38, 2341-2358.

20 Prokhorova, I. (2017) Aminoglycoside interactions and impacts on the eukaryotic ribosome. *PNAS*, in press.

21 Howard, M., Frizzell, R. A. and Bedwell, D. M. (1996) Aminoglycoside antibiotics restore CFTR function by overcoming premature stop mutations. *Nat Med*, 2, 467-469.

22 Bedwell, D. M., Kaenjak, A., Benos, D. J., Bebok, Z., Bubien, J. K., Hong, J., Tousson, A., Clancy, J. P. and Sorscher, E. J. (1997) Suppression of a CFTR premature stop mutation in a bronchial epithelial cell line. *Nat Med*, 3, 1280-1284.

23 Howard, M. T., Anderson, C. B., Fass, U., Khatri, S., Gesteland, R. F., Atkins, J. F. and Flanigan, K. M. (2004) Readthrough of dystrophin stop codon mutations induced by aminoglycosides. *Ann Neurol*, 55, 422-426.

24 Lai, C. H., Chun, H. H., Nahas, S. A., Mitui, M., Gamo, K. M., Du, L. and Gatti, R. A. (2004) Correction of ATM gene function by aminoglycoside-induced readthrough of premature termination codons. *Proc Natl Acad Sci USA*, 101, 15676-15681.

25 Pitcher, M. R., Herrera, J. A., Buffington, S. A., Kochukov, M. Y., Merritt, J. K., Fisher, A. R., Schanen, N. C., Costa-Mattioli, M. and Neul, J. L. (2015) Rett syndrome like phenotypes in the R255X Mecp2 mutant mouse are rescued by MECP2 transgene. *Hum Mol Genet*, 24, 2662-2672.

26 Vecsler, M., Ben Zeev, B., Nudelman, I., Anikster, Y., Simon, A. J., Amariglio, N., Rechavi, G., Baasov, T. and Gak, E. (2011) Ex vivo treatment with a novel synthetic aminoglycoside NB54 in primary fibroblasts from Rett syndrome patients suppresses MECP2 nonsense mutations. *PLoS One*, 6, e20733.

27 Lincoln, V., Cogan, J., Hou, Y., Hirsch, M., Hao, M., Alexeev, V., De Luca, M., De Rosa, L., Bauer, J. W., Woodley, D. T. et al. (2018) Gentamicin induces LAMB3 nonsense mutation readthrough and restores functional laminin 332 in junctional epidermolysis bullosa. *Proc Natl Acad Sci USA*, 115, E6536-e6545.

28 Keeling, K. M., Xue, X., Gunn, G. and Bedwell, D. M. (2014) Therapeutics based on stop codon readthrough. *Annu Rev Genomics Hum Genet*, 15, 371-394.

29 Karijolich, J. and Yu, Y. T. (2014) Therapeutic suppression of premature termination codons: mechanisms and clinical considerations (review). *Int J Mol Med*, 34, 355-362.

30 Namgoong, J. H. and Bertoni, C. (2016) Clinical potential of ataluren in the treatment of Duchenne muscular dystrophy. *Degener Neurol Neuromuscul Dis*, 6, 37-48.

31 Chen-Plotkin, A. S., Martinez-Lage, M., Sleiman, P. M., Hu, W., Greene, R., Wood, E. M., Bing, S., Grossman, M., Schellenberg, G. D., Hatanpaa, K. J. et al. (2011) Genetic and clinical features of progranulin-associated frontotemporal lobar degeneration. *Arch Neurol*, 68, 488-497.

32 Roy, B., Leszyk, J. D., Mangus, D. A. and Jacobson, A. (2015) Nonsense suppression by near-cognate tRNAs employs alternative base pairing at codon positions 1 and 3. *Proc Natl Acad Sci USA*, 112, 3038-3043.

33 Dunn, K. W., Kamocka, M. M. and McDonald, J. H. (2011) A practical guide to evaluating colocalization in biological microscopy. *Am J Physiol Cell Physiol*, 300, C723-742.

34 Hu, F., Padukkavidana, T., Vaegter, C. B., Brady, O. A., Zheng, Y., Mackenzie, I. R., Feldman, H. H., Nykjaer, A. and Strittmatter, S. M. (2010) Sortilin-mediated endocytosis determines levels of the frontotemporal dementia protein, progranulin. *Neuron*, 68, 654-667.

35 Floquet, C., Deforges, J., Rousset, J. P. and Bidou, L. (2011) Rescue of non-sense mutated p53 tumor suppressor gene by aminoglycosides. *Nucleic Acids Res*, 39, 3350-3362.

36 Bidou, L., Bugaud, O., Belakhov, V., Baasov, T. and Namy, O. (2017) Characterization of new-generation aminoglycoside promoting premature termination codon readthrough in cancer cells. *RNA Biol*, 14, 378-388.

37 Bosco, D. A., Lemay, N., Ko, H. K., Zhou, H., Burke, C., Kwiatkowski, T. J., Jr., Sapp, P., McKenna-Yasek, D., Brown, R. H., Jr. and Hayward, L. J. (2010) Mutant FUS proteins that cause amyotrophic lateral sclerosis incorporate into stress granules. *Hum Mol Genet*, 19, 4160-4175.

38 Gijselinck, I., Van Broeckhoven, C. and Cruts, M. (2008) Granulin mutations associated with frontotemporal lobar degeneration and related disorders: an update. *Hum Mutat*, 29, 1373-1386.

39 Yu, C. E., Bird, T. D., Bekris, L. M., Montine, T. J., Leverenz, J. B., Steinbart, E., Galloway, N. M., Feldman, H., Woltjer, R., Miller, C. A. et al. (2010) The spectrum of mutations in progranulin: a collaborative study screening 545 cases of neurodegeneration. *Arch Neurol*, 67, 161-170.

40 L, K. (2017) A Novel Loss-of-Function GRN Mutation p.(Tyr229*): Clinical and Neuropathological Features. *J Alzheimers Dis*, 55, 1167-1174.

41 Van Langenhove, T., van der Zee, J., Sleegers, K., Engelborghs, S., Vandenberghe, R., Gijselinck, I., Van den Broeck, M., Mattheijssens, M., Peeters, K., De Deyn, P. P. et al. (2010) Genetic contribution of FUS to frontotemporal lobar degeneration. *Neurology*, 74, 366-371.

42 Pacho, F., Zambruno, G., Calabresi, V., Kiritsi, D. and Schneider, H. (2011) Efficiency of translation termination in humans is highly dependent upon nucleotides in the neighbourhood of a (premature) termination codon. *J Med Genet*, 48, 640-644.

43 Floquet, C., Hatin, I., Rousset, J. P. and Bidou, L. (2012) Statistical analysis of readthrough levels for nonsense mutations in mammalian cells reveals a major determinant of response to gentamicin. *PLoS Genet*, 8, e1002608.

44 Bukowy-Bieryllo, Z., Dabrowski, M., Witt, M. and Zietkiewicz, E. (2016) Aminoglycoside-stimulated readthrough of premature termination codons in selected genes involved in primary ciliary dyskinesia. *RNA Biol*, 13, 1041-1050.

45 Lee, H. L. and Dougherty, J. P. (2012) Pharmaceutical therapies to recode nonsense mutations in inherited diseases. *Pharmacol Ther*, 136, 227-266.

46 Welch, E. M., Barton, E. R., Zhuo, J., Tomizawa, Y., Friesen, W. J., Trifillis, P., Paushkin, S., Patel, M., Trona, C. R., Hwang, S. et al. (2007) PTC124 targets genetic disorders caused by nonsense mutations. *Nature*, 447, 87-91.

47 Ryan, N. J. (2014) Ataluren: first global approval. *Drugs*, 74, 1709-1714.

48 Elia, L. P., Mason, A. R., Alijagic, A. and Finkbeiner, S. (2019) Genetic Regulation of Neuronal Progranulin Reveals a Critical Role for the Autophagy-Lysosome Pathway. *J Neurosci*, 39, 3332-3344.

49 Tanaka, Y., Suzuki, G., Matsuwaki, T., Hosokawa, M., Serrano, G., Beach, T. G., Yamanouchi, K., Hasegawa, M. and Nishihara, M. (2017) Progranulin regulates lysosomal function and biogenesis through acidification of lysosomes. *Hum Mol Genet*, 26, 969-988.

50 Gotzl, J. K., Colombo, A. V., Fellerer, K., Reifschneider, A., Werner, G., Tahirovic, S., Haass, C. and Capell, A. (2018) Early lysosomal maturation deficits in microglia triggers enhanced lysosomal activity in other brain cells of progranulin knockout mice. *Mol Neurodegener*, 13, 48.

51 Smith, K. R., Damiano, J., Franceschetti, S., Carpenter, S., Canafoglia, L., Morbin, M., Rossi, G., Pareyson, D., Mole, S. E., Staropoli, J. F. et al. (2012) Strikingly different clinicopathological phenotypes determined by progranulin-mutation dosage. *Am J Hum Genet*, 90, 1102-1107.

52 Holler, C. J., Taylor, G., Deng, Q. and Kukar, T. (2017) Intracellular Proteolysis of Progranulin Generates Stable, Lysosomal Granulins that Are Haploinsufficient in Patients with Frontotemporal Dementia Caused by GRN Mutations. *eNeuro*, 4.

53 Zhou, X., Paushter, D. H., Feng, T., Sun, L., Reinheckel, T. and Hu, F. (2017) Lysosomal processing of progranulin. *Mol Neurodegener*, 12, 62.

54 Zhou, X., Sun, L., Bastos de Oliveira, F., Qi, X., Brown, W. J., Smolka, M. B., Sun, Y. and Hu, F. (2015) Prosaposin facilitates sortilin-independent lysosomal trafficking of progranulin. *J Cell Biol*, 210, 991-1002.

55 Zhou, X., Sullivan, P. M., Sun, L. and Hu, F. (2017) The interaction between progranulin and prosaposin is mediated by granulins and the linker region between saposin B and C. *J Neurochem*, 143, 236-243.

56 Zheng, Y., Brady, O. A., Meng, P. S., Mao, Y. and Hu, F. (2011) C-terminus of progranulin interacts with the beta-propeller region of sortilin to regulate progranulin trafficking. *PLoS One*, 6, e21023.

57 Kuschal, C., DiGiovanna, J. J., Khan, S. G., Gatti, R. A. and Kraemer, K. H. (2013) Repair of UV photolesions in xeroderma pigmentosum group C cells induced by translational readthrough of premature termination codons. *Proc Natl Acad Sci USA*, 110, 19483-19488.

58 Gal, J., Strom, A. L., Kilty, R., Zhang, F. and Zhu, H. (2007) p62 accumulates and enhances aggregate formation in model systems of familial amyotrophic lateral sclerosis. *J Biol Chem*, 282, 11068-11077.

It will be understood that various details of the presently disclosed subject matter can be changed without departing from the scope of the subject matter disclosed herein. Furthermore, the foregoing description is for the purpose of illustration only, and not for the purpose of limitation.

The invention claimed is:

1. A method of inducing production of full-length pro-granulin (GRN) from a nucleotide sequence encoding a GRN mRNA with a premature stop codon (GRN-PTC), comprising exposing the GRN-PTC in a cell or a patient in need thereof to an agent selected from an effective amount of an aminoglycoside that yields full-length GRN.

2. The method of claim 1, wherein the aminoglycoside is selected from gentamicin or G418.

3. The method of claim 1, wherein the premature stop codon is R493X.

4. The method of claim 1, wherein the GRN nucleotide sequence is in a cell.

5. The method of claim 4, wherein the aminoglycoside is administered to the cell at a concentration between about 100 μg/mL and 2000 μg/mL.

6. The method of claim 4, wherein the cell is suffering from neurodegeneration.

7. The method of claim 6, wherein the cell is in a patient with frontotemporal dementia (FTD).

* * * * *

SEQUENCE LISTING

<160> NUMBER OF SEQ ID NOS: 8

<210> SEQ ID NO 1
<211> LENGTH: 20
<212> TYPE: DNA

```
<213> ORGANISM: Artificial Sequence
<220> FEATURE:
<223> OTHER INFORMATION: Beta Actin Forward Primer

<400> SEQUENCE: 1
agagctatga gctgcctgac                                                     20

<210> SEQ ID NO 2
<211> LENGTH: 20
<212> TYPE: DNA
<213> ORGANISM: Artificial Sequence
<220> FEATURE:
<223> OTHER INFORMATION: Beta Actin Reverse Primer

<400> SEQUENCE: 2
ggatgtcaac gtcacacttc                                                     20

<210> SEQ ID NO 3
<211> LENGTH: 23
<212> TYPE: DNA
<213> ORGANISM: Artificial Sequence
<220> FEATURE:
<223> OTHER INFORMATION: Progranulin Forward Primer

<400> SEQUENCE: 3
cgtgaaggct tgatcctgcg aga                                                 23

<210> SEQ ID NO 4
<211> LENGTH: 21
<212> TYPE: DNA
<213> ORGANISM: Artificial Sequence
<220> FEATURE:
<223> OTHER INFORMATION: Progranulin Reverse Primer

<400> SEQUENCE: 4
cttatcgtca tccttgtaat c                                                   21

<210> SEQ ID NO 5
<211> LENGTH: 23
<212> TYPE: DNA
<213> ORGANISM: Homo sapiens

<400> SEQUENCE: 5
cgtgaaggct tgatcctgcg aga                                                 23

<210> SEQ ID NO 6
<211> LENGTH: 23
<212> TYPE: DNA
<213> ORGANISM: Homo sapiens

<400> SEQUENCE: 6
cagtgggaag taaggctgct gcc                                                 23

<210> SEQ ID NO 7
<211> LENGTH: 23
<212> TYPE: DNA
<213> ORGANISM: Homo sapiens

<400> SEQUENCE: 7
gggtgccatc tagtgccctg ata                                                 23

<210> SEQ ID NO 8
<211> LENGTH: 23
<212> TYPE: DNA
<213> ORGANISM: Homo sapiens
```

```
<400> SEQUENCE: 8
tggaggcttc taggggggcc ggg                                            23
```